United States Patent [19]

Schwartz

[11] Patent Number: 4,650,417

[45] Date of Patent: Mar. 17, 1987

[54] DENTURE FORMING DEVICE

[76] Inventor: Robert Schwartz, 1271 Westfield Ave., Rahway, N.J. 07065

[21] Appl. No.: 322,568

[22] Filed: Nov. 18, 1981

Related U.S. Application Data

[63] Continuation-in-part of Ser. No. 114,096, Jan. 21, 1980, abandoned.

[51] Int. Cl.⁴ .............................................. A61C 13/10
[52] U.S. Cl. ................................................... 433/196
[58] Field of Search .................. 433/49, 196, 213, 34, 433/214; 206/83; 264/16, 17, 18; 269/254 DF; 164/DIG. 4; 249/54

[56] References Cited

U.S. PATENT DOCUMENTS

| | | | |
|---|---|---|---|
| 531,092 | 12/1894 | Boyd | 433/213 |
| 1,303,223 | 5/1919 | Wall | 433/196 |
| 1,339,821 | 5/1920 | Hall | 433/196 |
| 1,518,075 | 12/1924 | Kesling | 433/196 |
| 1,840,703 | 1/1932 | Cunningham | 433/71 |
| 2,229,780 | 1/1941 | Vaillancourt | 433/196 |
| 2,542,207 | 2/1951 | Osborne | 264/16 |
| 2,659,970 | 11/1953 | Ingersoll, Jr. | 264/18 |
| 2,859,088 | 11/1958 | Erdle et al. | 264/18 |
| 3,846,911 | 11/1974 | Wichner | 433/171 |

FOREIGN PATENT DOCUMENTS 510152  7/1939  United Kingdom ................ 433/213

Primary Examiner—John J. Wilson

[57] ABSTRACT

Dentures or denture elements made up of individual artificial teeth are formed using a structure that is adapted to receive at least the occlusal surface segments of anatomically adjacent artificial teeth of either the maxillary or mandibular arch and to retain such artificial teeth in a spaced relationship in conformance with an orthodontic or other standard arch form.

2 Claims, 3 Drawing Figures

DENTURE FORMING DEVICE

CROSS-REFERENCE TO RELATED APPLICATION

This application is a continuation-in-part of Ser. No. 114,096, filed Jan. 21, 1980, now abandoned.

BACKGROUND OF THE INVENTION

FIELD OF THE INVENTION

This invention is directed to a denture-forming device useful for preparing dental arches or dental arch elements from individual artificial teeth. More particularly, this invention is concerned with a device that can be used to prepare dental arches or segments of dental arches that correspond to standard orthodontic arch forms.

SUMMARY OF THE INVENTION

Artificial maxillary or mandibular arches, or segments thereof, that conform with orthodontic or other standard arch forms can be prepared with the device of the present invention. The denture forming device is preferably composed of a solid, mold-like structure that has tooth-positioning means formed into the upper surface thereof. The tooth positioning means are adapted to receive at least the occlusal surface segments of at least two anatomically adjacent artificial teeth of either the maxillary or mandibular arch. The tooth positioning means serves to retain such artificial teeth in a spaced-apart relationship in conformance with an orthodontic or other standard arch form. Most preferably, the denture-forming device positions individual teeth such that the buccal and/or labial extent of the individual teeth corresponds substantially to the line of a standard arch form.

BRIEF DESCRIPTION OF THE DRAWINGS

The invention will be more readily understood by reference to the accompanying drawings in which:

FIG. 2 is a cross-sectional view of a segment of the denture forming device of FIG. 1 taken along line A—A.

As is evident from FIG. 1, the denture forming device, in its simplest form, is a solid, mold-type structure 10 of holes or segments 1 that are adapted to retain and position individual artificial teeth substantially in conformance with an orthodontic arch form. The orthodontic arch form employed may be any of the standard arch forms such as the Grader; Bonwill-Hawley; Rock Mountain Data Systems; R. M. Ricketts, Ponts Index, etc. As shown in FIG. 2, holes or segments 1 are adapted to hold or position individual artificial teeth in a spaced-apart relationship relative to each other such that the buccal and/or labial surface thereof are held in conformance with a predetermined standard orthodontic arch form. Preferably the spacing between teeth is less than about one millimeter. The allowance of space in structure 10 between the segments allows for the vagaries in the mesial-distal width of the teeth provided by the teeth manufacturer.

For illustration, a standard orthodontic arch B is superimposed upon the upper surface of FIG. 1 to show the positioning of holes 1 of mold 10 relative to the desired arch form. While

The denture forming device can be formed from a variety of materials and the precise materials of construction used are not critical. Preferably the device is formed from a rubbery material that has good dimensional stability, such as silicone rubber or plasticized poly(vinyl chloride). In general, a different denture forming device is required for each different tooth manufacturer's product since the size and shape of individual artificial teeth vary from manufacturer to manufacturer.

Figure 1:
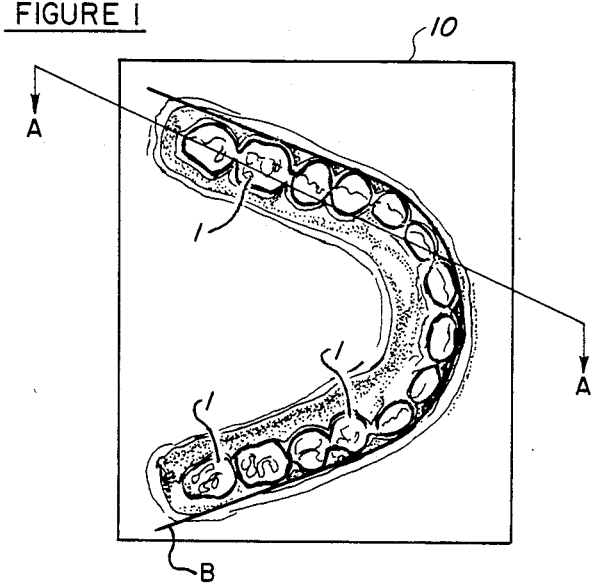
FIG. 1 shows a full maxillary arch, it should be recognized that similar devices having holes 1 to hold the less-than-full complement of teeth in the maxillary or mandibular arch are comtemplated by the present invention. Preferably, structure 10 retains the occlusal (lowermost) surfaces of the artificial teeth in substantially the same flat or spherical plane.
Figure 2:
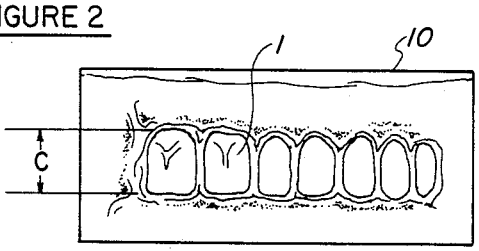
FIG. 2 is a top elevational view of a denture forming device of the present invention that is adapted to form a maxillary arch of artificial teeth.
Figure 3:
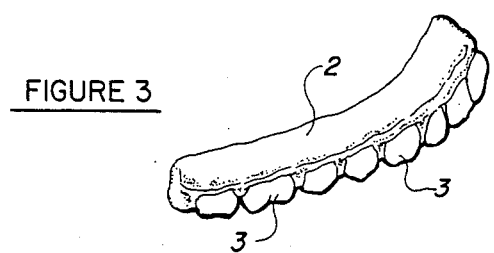
FIG. 3 is a view of a wax-up of a maxillary arch segment formed with the device of FIG. 1.

In use, the practitioner selects a denture forming device 10 constructed having holes 1 arranged to conform with the desired arch form, e.g., a number 5 Bonwill-Hawley arch form and will place either mandibular or maxillary teeth 3 into the various tooth holding compartments 1 of device 10. These tooth holding compartments 1 are adapted to retain each individual artificial tooth 3 in a spaced-apart relationship relative to each other and in conformance with the orthodontic arch form. As shown in FIG. 2, compartment 1 is designed to retain the occlusal surface of each individual tooth in the bottom portion of each compartment 1. The bottom of each compartment 1 may be relatively flat. Preferably each compartment 1 is sized such that the lower portion (nearest the occlusal surface) of each tooth is held securely in place. Preferably each compartment 1 encloses the lower portion of each tooth to a height C (see FIG. 2) such that the buccal and/or facial and lingual and/or palatal surface of each artificial tooth is not enclosed beyond a point immediately above the undercut point of each artifical tooth in situations where the manufacturer has provided the undercut. Thereafter the practitioner will typically place wax or other binding medium (thermoplastics) 2 over the non-enclosed portions of the individual teeth 3 to bind them together in a complete arch or arch segment (see FIG. 3). If wax is used, minor adjustments of individual teeth in the completed arch may be made readily. This product, after removal from device 10, is thereafter used in the manufacture of artificial dentures. Using the device of the present invention permits the practitioner to form maxilary or mandibular arches that conform substantially to standard arch forms, from individual artificial teeth. The arches are precise, readily formed and possess the esthetices normally associated with dentures formed from individual artificial teeth.

What is claimed is:

1. A denture forming device comprising a solid structure having individual tooth holding compartments formed into the upper surface thereof for at least two anatomically adjacent individual artificial teeth of the maxillary or mandibular arch, each compartment adapted to receive and enclose the occlusal surface of said teeth in substantially the same flat or spherical plane and to retain the teeth in a spaced-apart relationship relative to each other such that the buccal and/or labial surface of said artificial teeth are held in conformance with a standard orthodontic arch form.

2. The denture forming device of claim 1 wherein the spacing between said individual artificial teeth is less than about 1 millimeter.

* * * * *